United States Patent
Wong et al.

(10) Patent No.: US 7,481,536 B2
(45) Date of Patent: Jan. 27, 2009

(54) METHODS AND SYSTEMS FOR DIFFERENTIATING LEFT AND RIGHT EYE IMAGES

(75) Inventors: Jonathan Wong, Milpitas, CA (US); Dimitri Chernyak, Sunnyvale, CA (US)

(73) Assignee: AMO Manufacturing USA, LLC, Santa Clara, CA (US)

( * ) Notice: Subject to any disclaimer, the term of this patent is extended or adjusted under 35 U.S.C. 154(b) by 721 days.

(21) Appl. No.: 10/784,481

(22) Filed: Feb. 19, 2004

(65) Prior Publication Data

US 2005/0185138 A1    Aug. 25, 2005

(51) Int. Cl.
    *A61B 3/00*    (2006.01)
(52) U.S. Cl. .................. 351/246; 351/204; 351/206
(58) Field of Classification Search ............ 351/246
    See application file for complete search history.

(56) References Cited

U.S. PATENT DOCUMENTS

| | | | |
|---|---|---|---|
| 4,365,874 A | 12/1982 | Milburn et al. | |
| 4,540,254 A | 9/1985 | Humphrey | |
| 4,641,349 A | 2/1987 | Flom et al. | |
| 4,665,913 A | 5/1987 | L'Esperance, Jr. | |
| 4,761,071 A | 8/1988 | Baron | |
| 4,815,839 A | 3/1989 | Waldorf | |
| 4,848,340 A | 7/1989 | Bille et al. | |
| 4,995,716 A | 2/1991 | Warnicki et al. | |
| 5,144,630 A | 9/1992 | Lin | |
| 5,163,934 A | 11/1992 | Munnerlyn | |
| 5,196,873 A | 3/1993 | Yamanobe et al. | |
| 5,219,344 A | 6/1993 | Yoder | |
| 5,231,674 A | 7/1993 | Cleveland et al. | |
| 5,280,312 A | 1/1994 | Yamada et al. | |
| 5,291,231 A | 3/1994 | Hideshima et al. | |
| 5,291,560 A | 3/1994 | Daugman | |
| 5,341,180 A | 8/1994 | Isogai et al. | |
| 5,347,331 A | 9/1994 | Isogai et al. | |
| 5,398,684 A | 3/1995 | Hardy | |
| 5,406,342 A | 4/1995 | Jongsma | |
| 5,491,524 A | 2/1996 | Hellmuth et al. | |
| 5,614,967 A | 3/1997 | Ishikawa et al. | |
| 5,632,742 A | 5/1997 | Frey et al. | |
| 5,646,791 A | 7/1997 | Glockler | |
| 5,683,379 A | 11/1997 | Hohla | |
| 5,713,892 A | 2/1998 | Shimmick | |
| 5,737,058 A | 4/1998 | Umemura et al. | |
| 5,740,803 A | 4/1998 | Gray et al. | |
| 5,742,626 A | 4/1998 | Mead et al. | |

(Continued)

*Primary Examiner*—Jessica T Stultz
(74) *Attorney, Agent, or Firm*—Townsend and Townsend and Crew LLP (57) ABSTRACT

Methods and systems for determining whether an image is of a left eye or a right eye may be used to enhance laser eye surgery systems and techniques. Methods generally involve locating an iris center and/or pupil center on an image of the eye, locating a corneal vertex and/or at least one reflection on the image, and determining whether the image is of a left eye or a right eye, based on the location of the corneal vertex and/or reflection(s) relative to the iris center and/or pupil center. Systems include a laser emitting a beam of an ablative light energy and a computer processor having a computer program for determining whether the image is of a left eye or a right eye, based on a location of the corneal vertex and/or reflection(s) relative to the iris center and/or pupil center.

25 Claims, 5 Drawing Sheets

U.S. PATENT DOCUMENTS

| | | | |
|---|---|---|---|
| 5,757,462 | A | 5/1998 | Nanjo |
| 5,777,719 | A | 7/1998 | Williams et al. |
| 5,790,235 | A | 8/1998 | Kirschbaum |
| 5,822,446 | A | 10/1998 | Kato |
| 5,843,070 | A | 12/1998 | Cambier et al. |
| 5,912,775 | A | 6/1999 | Glockler |
| 5,912,779 | A | 6/1999 | Llewellyn et al. |
| 5,980,513 | A | 11/1999 | Frey et al. |
| 5,982,555 | A | 11/1999 | Melville et al. |
| 6,004,313 | A | 12/1999 | Shimmick et al. |
| 6,042,012 | A | 3/2000 | Olmstead et al. |
| 6,095,651 | A | 8/2000 | Williams et al. |
| 6,099,522 | A | 8/2000 | Knopp et al. |
| 6,116,738 | A | 9/2000 | Rorabaugh |
| 6,129,722 | A | 10/2000 | Ruiz |
| 6,159,202 | A | 12/2000 | Sumiya et al. |
| 6,199,986 | B1 | 3/2001 | Williams et al. |
| 6,203,539 | B1 | 3/2001 | Shlmmldc et al. |
| 6,217,570 | B1 | 4/2001 | Nevyas |
| 6,217,915 | B1 | 4/2001 | Luchansky et al. |
| 6,245,059 | B1 | 6/2001 | Clapham |
| 6,257,722 | B1 | 7/2001 | Toh |
| 6,267,756 | B1 | 7/2001 | Feuerstein et al. |
| 6,271,914 | B1 | 8/2001 | Frey et al. |
| 6,271,915 | B1 | 8/2001 | Frey et al. |
| 6,280,435 | B1 | 8/2001 | Odrich et al. |
| 6,280,436 | B1 | 8/2001 | Freeman et al. |
| 6,285,780 | B1 | 9/2001 | Yamakita et al. |
| 6,302,876 | B1 | 10/2001 | Shimmick et al. |
| 6,315,413 | B1 | 11/2001 | Shlmmlck et al. |
| 6,319,247 | B1 | 11/2001 | Hofer et al. |
| 6,331,177 | B1 | 12/2001 | Munnerlyn et al. |
| 6,396,069 | B1 | 5/2002 | MacPherson et al. |
| 6,467,907 | B1 | 10/2002 | Fujieda et al. |
| 6,497,483 | B2 | 12/2002 | Frey et al. |
| 6,526,161 | B1 | 2/2003 | Yan |
| 6,530,917 | B1 | 3/2003 | Seiler et al. |
| 6,546,121 | B1 | 4/2003 | Oda |
| 6,572,606 | B2 | 6/2003 | Kliewer et al. |
| 6,585,724 | B2 | 7/2003 | Toh |
| 6,607,527 | B1 | 8/2003 | Ruiz et al. |
| 6,685,320 | B2 * | 2/2004 | Hirohara et al. ............. 351/221 |
| 6,730,074 | B2 | 5/2004 | Bille et al. |
| 6,866,661 | B2 | 3/2005 | Gray et al. |
| 2002/0013573 | A1 | 1/2002 | Telfair et al. |
| 2002/0047992 | A1 | 4/2002 | Graves et al. |
| 2002/0049431 | A1 | 4/2002 | Smith et al. |
| 2003/0076477 | A1 | 4/2003 | Matsumoto |
| 2003/0105457 | A1 | 6/2003 | Mrochen et al. |
| 2004/0169817 | A1 | 9/2004 | Grotehusmann et al. |

* cited by examiner

METHODS AND SYSTEMS FOR DIFFERENTIATING LEFT AND RIGHT EYE IMAGES

CROSS-REFERENCE TO RELATED APPLICATIONS

The present application is related to U.S. patent application Ser. No. 10/300,714, filed Nov. 19, 2002, and Ser. No. 10/460,060, filed Jun. 11, 2003, the full disclosures of which are hereby incorporated by reference.

BACKGROUND OF THE INVENTION

The present invention relates generally to laser eye surgery methods and systems. More specifically, the present invention relates to methods and systems for differentiating between left and right eye images.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, thermal shaping, and the like.

Known corneal correction treatment methods have generally been successful in correcting standard vision errors, such as myopia, hyperopia, astigmatism, and the like. By customizing an ablation pattern based on wavefront measurements, it may be possible to correct minor aberrations to reliably and repeatedly provide visual acuity greater than 20/20. Methods and systems for providing wavefront measurements continue to benefit from improvements and advancements, such as those described in U.S. patent application Ser. Nos. 10/300,714 and 10/460,060 (incorporated above by reference). Of course, wavefront measurement systems alone cannot eliminate all potential error from a laser eye surgery procedure. Errors may occur, for example, in transferring information from the measurement system to the ablation system or in the operation of the ablation system. One possible error that may be made is that a wavefront measurement image of a left eye may be confused with a wavefront image of a right eye. This may occur due to a mislabeling of the images, misinterpretation of the images by an operator of the ablation system, or the like. In a worst case scenario, wavefront measurement data for left and right eyes may accidentally be reversed, so that the treatment for the left eye is performed on the right eye and vice versa.

Therefore, it would be desirable to provide methods and systems for differentiating between left and right eye images. Ideally, such methods and systems would differentiate left and right eye images acquired using wavefront imaging technology and would reduce the likelihood of human error in a laser eye surgery procedure.

BRIEF SUMMARY OF THE INVENTION

In one aspect of the present invention, a method of determining whether an image of an eye is of a left eye or a right eye involves locating an iris center on the image, locating a corneal vertex on the image, and determining whether the image is of a left eye or a right eye, based on the location of the corneal vertex relative to the iris center. Some embodiments further include locating a center of the pupil of the eye on the image before locating the center of the iris. In some embodiments, locating the corneal vertex involves locating at least one reflection on the image, the reflection having been caused by illuminating the eye while acquiring the image. In some embodiments, determining whether the image is of a left eye or a right eye may involve assuming that the at least one reflection is displaced, relative to the iris center, toward the nose of the patient from whom the image was acquired. In such embodiments, the determination step may further include measuring a displacement of the at least one reflection toward the nose, relative to the iris center and determining whether the image is of the left eye or the right eye, based on the measured displacement. Alternatively, the determining step may include: measuring a displacement of the at least one reflection toward the nose, relative to the iris center; comparing the measured displacement with a predetermined threshold displacement; and determining whether the image is of the left eye or the right eye only if the measured displacement is equal to or greater than the predetermined threshold.

Optionally, the method may further include illuminating the eye and obtaining the image of the eye before the locating steps. In some embodiments, the eye is illuminated with at least one infrared light source. For example, the pupil of the eye may be illuminated with at least two infrared light emitting diodes disposed near an opening through which the image is acquired. In some embodiments, the eye image is obtained using a wavefront imaging device. Again, in some such embodiments an image of the pupil of the eye may be obtained, and illuminating the eye may optionally involve illuminating the pupil using at least one infrared light source disposed near an opening through which the eye image is acquired. In some embodiments, the method may further involve performing a customized laser eye surgery procedure on the eye, based on the determination of whether the image is of a left eye or a right eye.

In another aspect of the present invention, a method of determining whether an image of an eye is of a left eye or a right eye involves locating a pupil center on the image, locating a corneal vertex on the image, and determining whether the image is of a left eye or a right eye, based on the location of the corneal vertex relative to the pupil center. Again, in some embodiments locating the corneal vertex involves locating at least one reflection on the image, with the at least one reflection being caused by illuminating the eye while acquiring the image. Any of the features described above may suitably apply to various embodiments of this aspect of the invention.

In yet another aspect of the invention, a method of determining whether an image of an eye is of a left eye or a right eye comprises locating an iris center on the image, locating at least one reflection on the image, and determining whether the image is of a left eye or a right eye, based on the location of the at least one reflection relative to the iris center. As with the embodiments discussed above, the reflection(s) are caused by illuminating the eye while acquiring the image. Again, this method may include any of the features described above.

In another aspect of the invention, a method of performing laser eye surgery comprises: acquiring a wavefront measurement of an eye; obtaining an image of the eye during the wavefront measurement; generating a treatment for the eye based on the wavefront measurement; determining whether the image is of a left eye or a right eye, based on nasally-directed displacement of a corneal vertex on the image relative to an iris center on the image; and verifying that a correct eye has been selected on which to perform a laser eye surgery procedure, based on the determination of whether the image is of a left eye or a right eye. In some embodiments, the step of determining whether the image of the eye is of a left eye or a right eye involves: locating the iris center on the image; locating the corneal vertex on the image; and comparing the location of the corneal vertex to the location of the iris center.

As mentioned above, in some embodiments the pupil of the eye may first be located before locating the iris center. Also in some embodiments, locating the corneal vertex may involve locating at least one reflection on the image, wherein the at least one reflection is caused by illuminating the eye while acquiring the image. In some embodiments, determining whether the image is of a left eye or a right eye may involve assuming that the at least one reflection is displaced, relative to the iris center, toward a nose of a patient from whom the image was acquired. The determination step may optionally include measuring a displacement of the at least one reflection toward the nose, relative to the iris center and determining whether the image is of the left eye or the right eye, based on the measured displacement. Alternatively, the determination step may involve: measuring a displacement of the at least one reflection toward the nose, relative to the iris center; comparing the measured displacement with a predetermined threshold displacement; and determining whether the image is of the left eye or the right eye only if the measured displacement is equal to or greater than the predetermined threshold.

Various embodiments involve illuminating the eye with one or more illumination devices such as infrared lights, as described above. In some embodiments the pupil is illuminated with two infrared lights that form the reflections on the image as just described.

In another aspect of the invention, a laser eye surgery system includes a laser emitting a beam of an ablative light energy and a computer processor configured to receive an image of an eye and at least one of a wavefront measurement and an ablation pattern for the eye, the computer processor having a computer program for determining whether the image is of a left eye or a right eye, based on a location of corneal vertex on the image relative to an iris center on the image. The computer processor is configured to verify that a correct eye has been selected on which to perform a laser eye surgery procedure, based on the determination and on the wavefront measurement and/or ablation pattern. In some embodiments, the image of the eye comprises a pupil image taken during the wavefront measurement.

Optionally, the computer processor may be further configured to locate the iris center and the corneal vertex on the image. For example, the computer processor may determine the location of the corneal vertex based on a location of at least one reflection on the image, with the at least one reflection being caused by illuminating the eye while acquiring the image. In some embodiments, the computer processor determines whether the image is of the left eye or the right eye by assuming that the reflection is located closer than the iris center to a nose of a patient from whom the image was obtained. In some embodiments, the computer processor is further configured to measure a distance between the iris center and the at least one reflection. Optionally, the computer processor may be further configured to compare the measured distance to a predetermined threshold distance and decide whether a left-eye/right-eye determination can be made, based on the comparison.

In some embodiments, the system further includes at least one image acquisition device for obtaining the image. For example, the image acquisition device may comprise a wavefront imaging device for imaging a pupil of the eye. In some embodiments, the wavefront imaging device includes at least one infrared light source disposed near an opening through which the pupil image is acquired.

In another aspect of the present invention, a laser eye surgery system includes: a laser emitting a beam of an ablative light energy; a light source directing light toward a corneal tissue of the eye; a microscope capturing an image of the illuminated corneal tissue; and a computer processor configured to direct a customized pattern of the ablative light energy toward the eye, the processor having a left/right eye identification module generating either a left eye signal or a right eye signal in response to the corneal tissue image. In some embodiments, the module generates an indeterminate eye signal when the corneal tissue image provides insufficient information for generating a left eye signal or a right eye signal. For example, the insufficient information may comprise an amount of displacement of a corneal vertex location of the eye relative to an iris center of the eye, the amount of displacement being less than a predetermined threshold amount. In some embodiments, the processor verifies that a correct eye has been selected on which to perform a laser eye surgery procedure, based on the left eye or right eye signal and on at least one of a wavefront measurement and an ablation pattern for the eye.

Further aspects and embodiments of the invention are described in greater detail below, with reference to the attached drawing figures.

DETAILED DESCRIPTION OF THE INVENTION

The present invention is particularly useful for enhancing the safety and accuracy of laser eye surgical procedures such as photorefractive keratectomy (PRK), phototherapeutic keratectomy (PTK), laser in situ keratomileusis (LASIK), and the like. Safety and accuracy is enhanced by distinguishing right eye images from left eye images, to help ensure that an eye treatment plan is matched with a proper eye. While the system and methods of the present invention are described primarily in the context of improving laser eye surgery methods and systems, various embodiments may also be adapted for use in alternative eye treatment procedures and systems such as femtosecond lasers and laser treatment, infrared lasers and laser treatments, radial keratotomy (RK), scleral bands, follow up diagnostic procedures, and the like.

Figure 1:
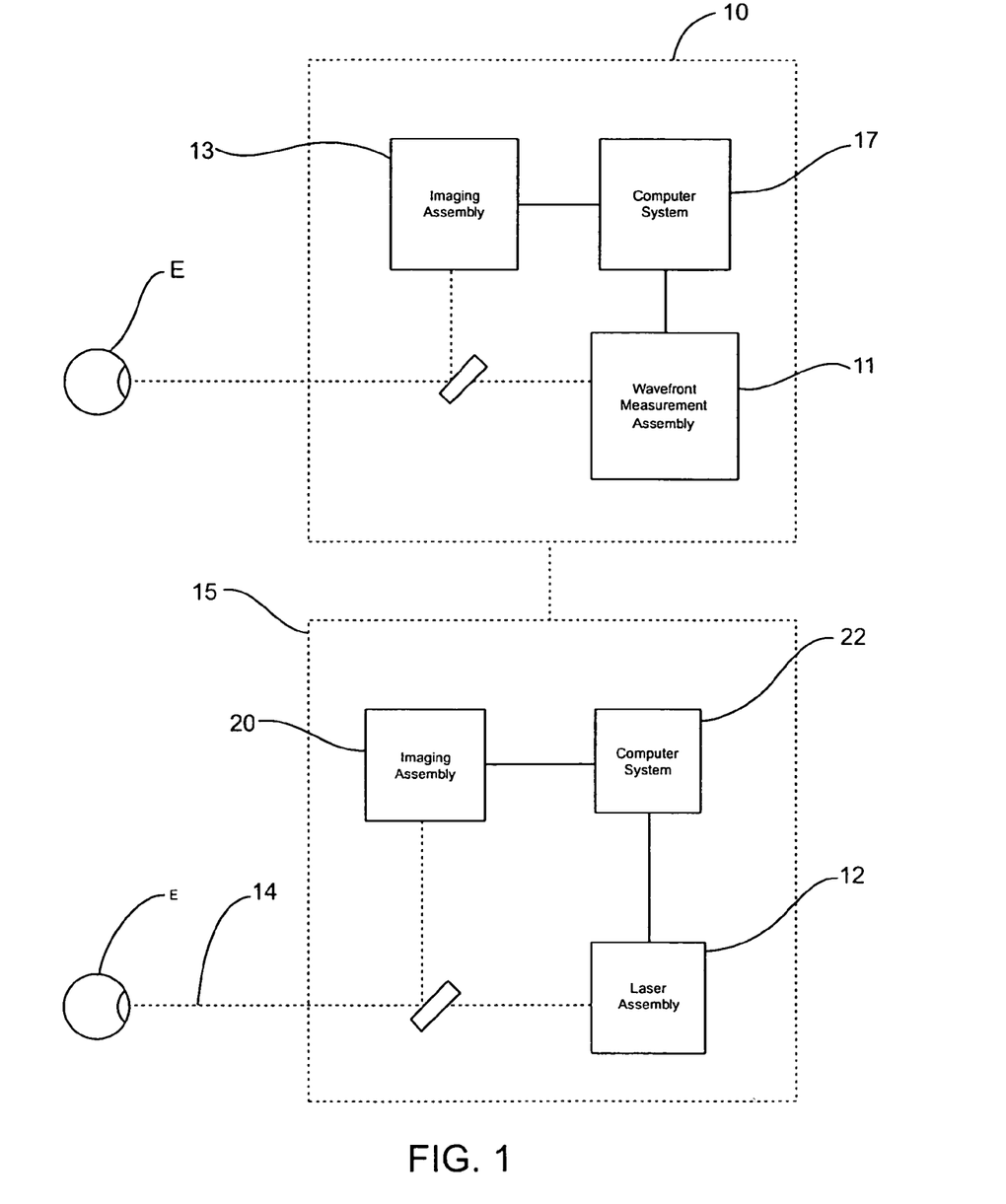
FIG. 1 schematically illustrates a simplified laser eye surgery system according to one embodiment of the present invention.

Referring to FIG. 1, one embodiment of a system for performing laser eye surgery includes a laser system 15 coupled to a wavefront measurement device 10 that measures aberrations and other optical characteristics of an entire optical tissue system. The data from such a wavefront measurement device may be used to generate an optical surface from an array of optical gradients. The optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients should correct the optical tissue system. As used herein terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium, Bowman's membrane and stroma to be displaced and expose the underlying stroma during a LASIK procedure).

Figure 2:
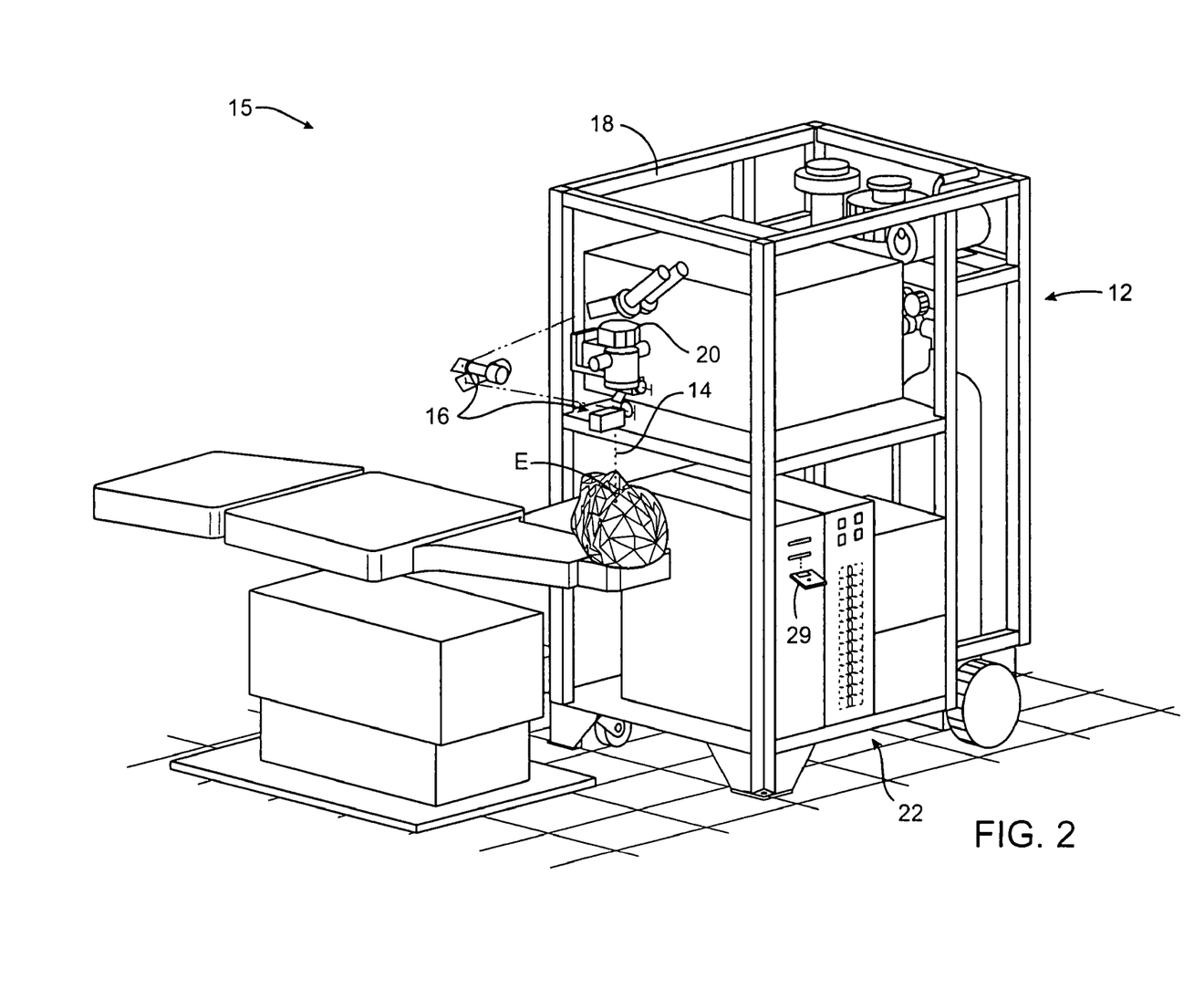
FIG. 2 is a perspective/schematic view of a laser surgery system according to one embodiment of the present invention.

Referring now to FIGS. 1 and 2, one embodiment of laser eye surgery system 15 includes a laser 12 that produces a laser beam 14. Laser 12 is optically coupled to laser delivery optics 16, which direct laser beam 14 to an eye E of a patient. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, typically comprising an argon-fluorine laser producing pulses of laser light having a wavelength of approximately 193 nm. Laser 12 will preferably be designed to provide a feedback stabilized fluence at the patient's eye E, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye E under the direction of a computer processor 22. Processor 22 will generally selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process so as to deliver the customized ablation profile, with the processor ideally altering the ablation procedure in response to inputs from the optical feedback system. The feedback will preferably be input into processor 22 from an automated image analysis system, or may be manually input into the processor by a system operator using an input device in response to a visual inspection of analysis images provided by the optical feedback system. Processor 22 will often continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference) and as demonstrated by other scanning laser systems such as the LSX laser by LaserSight, LadarVision by Alcon/Autonomous, and the 217C by Technolas; using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 15. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As mentioned above, laser system 15 will generally include a computer system or programmable processor 22. Processor 22 may comprise (or interface with) a conventional PC system including the standard user interface devices such as a keyboard, a display monitor, and the like. Processor 22 will typically include an input device such as a magnetic or optical disk drive, a CD drive, an internet connection, or the like. Such input devices will often be used to download a computer executable code from a computer network or a tangible storage media 29 embodying steps or programming instructions for any of the methods of the present invention. Tangible storage media 29 includes, but is not limited to a CD-R, a CD-RW, DVD, a floppy disk, an optical disk, a data tape, a non-volatile memory, or the like, and the processor 22 will include the memory boards and other standard components of modern computer systems for storing and executing this code.

Wavefront measurement device 10 typically includes a wavefront measurement assembly 11 and an imaging assembly 13. Wavefront measurement assembly 11 can be used to measure and obtain a wavefront elevation surface of at least one of the patient's eyes, and imaging assembly 13 can obtain still or moving images of the patient's eye during the wavefront measurement.

In exemplary embodiments, imaging assembly 13 is a CCD camera that can obtain a still image of the patient's eye. The image(s) obtained by imaging assembly 13 can thereafter be used to register the wavefront measurement and/or a customized ablation pattern (based on the wavefront measurement) with the patient's eye during the laser surgical procedure. Various embodiments and features of imaging assembly 13 are described in greater detail below.

The wavefront measurement assembly 11 and imaging assembly 13 can be coupled to or integral with a computer system 17 that can generate and store the wavefront measurements and images of the patient's eye. Thereafter, the patient's wavefront data can be stored on a computer readable medium, such as a CD-R, CD-RW, DVD-R, floppy disk, optical disk, a hard drive, or other computer readable medium. Optionally, in some embodiments, the computer system of the wavefront measurement device can generate and save an ablation profile based on the wavefront data.

The wavefront data and/or the customized ablation profile can be loaded into a laser surgical system 15 through reading of the computer readable medium or through delivery into a memory of surgical system 15 over a local or wide-area network (LAN or WAN). Laser eye surgery system 15 can include a computer controller system 22 that is in communication with an imaging assembly 20 and a laser assembly 12. Computer system 22 can have software stored in a memory and hardware that can be used to control the delivery of the ablative energy to the patient's eye, the tracking of the position (translations in the x, y, and z directions and torsional rotations) of the patient's eye relative to an optical axis of laser beam 14, and the like. In exemplary embodiments, among other functions, computer system 22 can be programmed to calculate a customized ablation profile based on the wavefront data, register the image(s) taken with wavefront measurement assembly 11 with the image(s) taken by imaging assembly 20, and measure the torsional offset between the patient's eye in the two images. Additionally, computer system 22 can be programmed to measure, in real-time, the movement (x(t), y(t), z(t), and rotational orientation) of the patient's eye relative to the optical axis of the laser beam so as to allow the computer system to modify the delivery of the customized ablation profile based on the real-time position of the patient's eye. Such features are described more fully in U.S. patent application Ser. No. 10/300,714, which was previously incorporated by reference.

Figure 3:
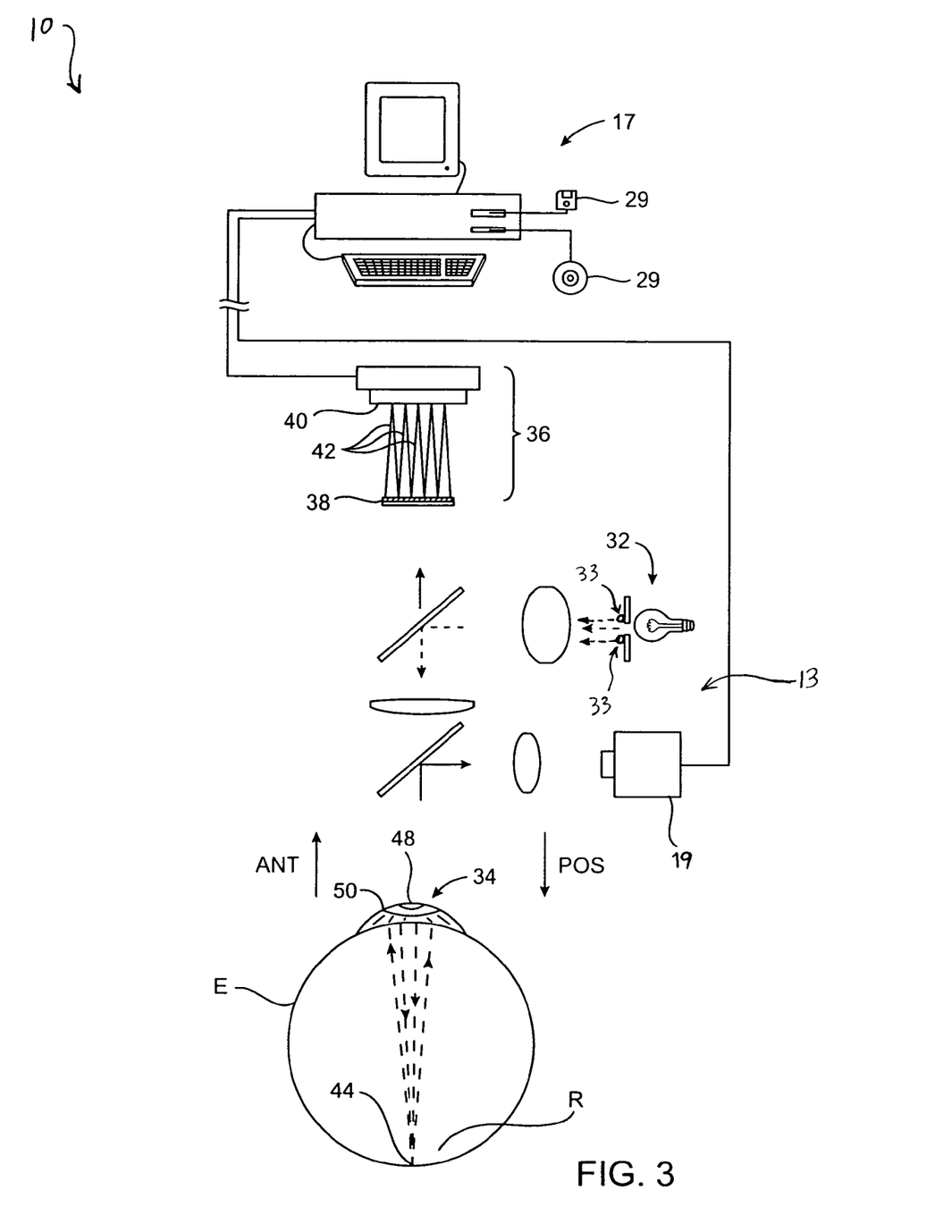
FIG. 3 is a diagram of a wavefront measurement device according to one embodiment of the present invention.

Referring now to FIG. 3, one embodiment of a wavefront measurement device 10 of the present invention is schematically illustrated. The illustrated embodiment is merely an example of one wavefront measurement device 10, and any of a number of other conventional or proprietary wavefront measurement devices may be used with various embodiments of the present invention.

Generally, wavefront measurement device 10 includes an imaging assembly 13 that can image the patient's eye E during the wavefront measurement. Imaging assembly 13 includes an image source 32 which projects a source image through optical tissues 34 of eye E to form an image 44 upon a surface of retina R. The image from retina R is transmitted by the optical system of the eye (specifically, optical tissues 34) and imaged onto a wavefront sensor 36 by system optics 38.

In some embodiments, imaging assembly 13 further includes a pupil camera 19, which may be used to acquire one or more pupil images of the eye E. Pupil images are images of the iris of the eye E, typically acquired with infrared (IR) illumination. Such images may be used, for example, to determine the size of the pupil of the eye E, to compare iris and pupil locations, to register iris and pupil locations for treatment and/or the like. In some embodiments, one or more (preferably two) infrared (IR) light emitting diodes (LEDs) 33 are disposed on opposites sides of an opening through which image source 32 projects its source image. IR LEDs generally provide IR illumination for acquiring the pupil images. The IR illumination produces distinct reflections on the corneal surface of the eye E, which are visible on each pupil image acquired.

Pupil camera 13 may be in communication with a computer system 17 to deliver the image(s) of the patient's eye E to a memory in computer 17. In various embodiments, computer system 17 may determine a location of the pupil of the eye on the pupil image and use that location to determine a location of the center of the iris of the eye. Techniques for determining an iris center location are described more fully in U.S. patent application Ser. No. 10/300,714, previously incorporated by reference. The computer 17 may further determine the location(s) of one or more reflections (Perkinje images) on a pupil image, caused by the IR illumination, and use the reflection location(s) to determine a location of a corneal vertex of the eye E. Techniques for determining a corneal vertex location are described more fully in U.S. patent application Ser. No. 10/460,060, which was also previously incorporated by reference. Next, the computer may compare either the corneal vertex location, the location of one or more reflections, or both with the iris center location. It has been found that the location of the reflections and/or the corneal vertex are typically nasally displaced relative to the iris center in an eye. In other words, the computer system 17 may assume that a reflection and/or a corneal vertex on a pupil image is closer to the patient's nose than the iris center is. By comparing the reflection and/or corneal vertex location to the iris location, the computer system 17 can determine if a given pupil image is of a left eye or a right eye.

The location of the optical axis of the eye E may also be verified by reference to the data provided from pupil camera 19. In the exemplary embodiment, pupil camera 19 images pupil 50 and/or the iris so as to allow subsequent determination of a position and torsional orientation of the pupil and/or iris for registration of the wavefront sensor data relative to the optical tissues, as is described more fully in U.S. patent application Ser. No. 10/300,714, previously incorporated by reference.

Wavefront sensor 36 can also communicate signals to computer 17 for determination of a corneal ablation treatment program. Computer 17 may be the same computer which is used to direct operation of the laser surgery system 15, or at least some or all of the computer components of the wavefront measurement device 10 and laser surgery system may be separate. Data from wavefront sensor 36 may be transmitted to laser system computer 22 (FIG. 1) via tangible media 29, via an I/O port, via an networking connection such as an intranet, the Internet, or the like.

Wavefront sensor 36 generally comprises a lenslet array 38 and an image sensor 40. As the image from retina R is transmitted through optical tissues 34 and imaged onto a surface of lenslet array 38, the lenslet array separates the transmitted image into an array of beamlets 42, and (in combination with other optical components of the system) images the separated beamlets on the surface of sensor 40. Sensor 40 typically comprises a charge coupled device (CCD) and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. In some embodiments, image source projection optics (not shown) may be configured or adapted to decrease any distortion of image 44.

In some embodiments, image source optics may decrease lower order optical errors by compensating for spherical and/or cylindrical errors of optical tissues 34. Higher order optical errors of the optical tissues may also be compensated through the use of an adaptive optic element, such as a deformable mirror. Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have well-defined and accurately formed image 44 on retina R.

While the method of the present invention will generally be described with reference to sensing of an image 44 on the retina, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront device 10 by focusing on a fixation target, as described in U.S. Pat. No. 6,004,313, the full disclosure of which is incorporated herein by reference. By varying a focal position of the fixation target as described in that reference, optical characteristics of the eye may be determined while the eye accommodate or adapts to image a field of view at a varying distance. Further alternatives include rotating of the eye by providing alternative and/or moving fixation targets within wavefront device 10.

Figure 3A:
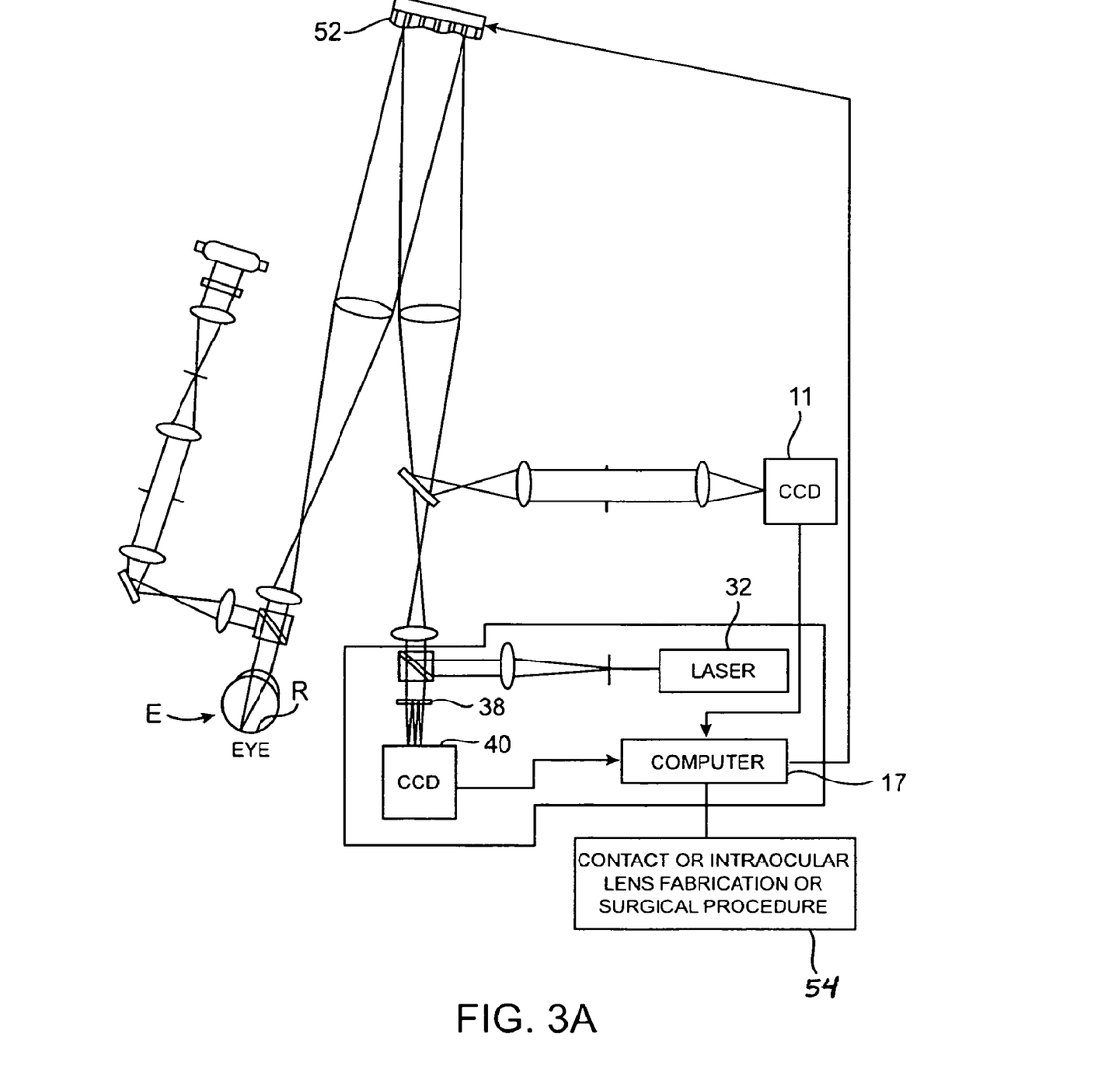
FIG. 3A is a diagram of an alternative wavefront measurement device according to another embodiment of the present invention.

An alternative embodiment of a wavefront sensor system is illustrated in FIG. 3A. The major components of the system of FIG. 3A are similar to those of FIG. 3. Additionally, FIG. 3A includes an adaptive optical element 52 in the form of a deformable mirror. The source image is reflected from deformable mirror 52 during transmission to retina R, and deformable mirror 52 is also along the optical path used to form the transmitted image between retina R and imaging sensor 40. Deformable mirror 52 can be controllably deformed to limit distortion of the image formed on the retina, and may enhance the accuracy of the wavefront data. The structure and use of the system of FIG. 3A are more fully described in U.S. Pat. No. 6,095,651, the full disclosure of which his incorporated herein by reference.

The components of one embodiment of a wavefront system for measuring the eye and ablations comprise elements of a VISX WaveScan®, available from VISX, Incorporated of Santa Clara, Calif. A preferred embodiment includes a WaveScan with a deformable mirror as described above. An alternate embodiment of a wavefront measuring device is described in U.S. Pat. No. 6,271,915, the full disclosure of which is incorporated herein by reference.

A treatment program map may be calculated from the wavefront elevation map so as to remove the regular (spherical and/or cylindrical) and irregular errors of the optical tissues. By combining the treatment program with a laser ablation pulse characteristics of a particular laser system, a table of ablation pulse locations, sizes, shapes, and/or numbers can be developed. An exemplary method and system for preparing such an ablation table is described in co-pending U.S. patent application Ser. No. 09/805,737 filed on Mar. 13, 2001 and entitled "Generating Scanning Spot Locations for Laser Eye Surgery," the full disclosure of which is incorporated herein by reference. Ablation table may optionally be optimized by sorting individual pulses to avoid localized heating, minimize irregular ablations if the treatment program is interrupted, and the like.

Based on the wavefront measurements of the eye, a corneal ablation pattern may be calculated by computer processor 17 or 22 (or by another separate processor) for ablating the eye with laser ablation system 15 to correct the optical errors of the eye. Such calculations will often be based on both the measured optical properties of the eye and on the characteristics of the corneal tissue targeted for ablation (such as the ablation rate and the refractive index). The results of the calculation will often comprise an ablation pattern in the form of an ablation table listing ablation locations, numbers of pulses, ablation sizes, and or ablation shapes to effect the desired refractive correction. An exemplary method for generating ablation patterns is described in co-pending U.S. patent application Ser. No. 09/805,737, the full disclosure of which was previously incorporated herein by reference. Where the refractive error is to be corrected by alternative treatment modalities, alternative treatment plans may be prepared, such as a corneal implant or the like.

Figure 4:
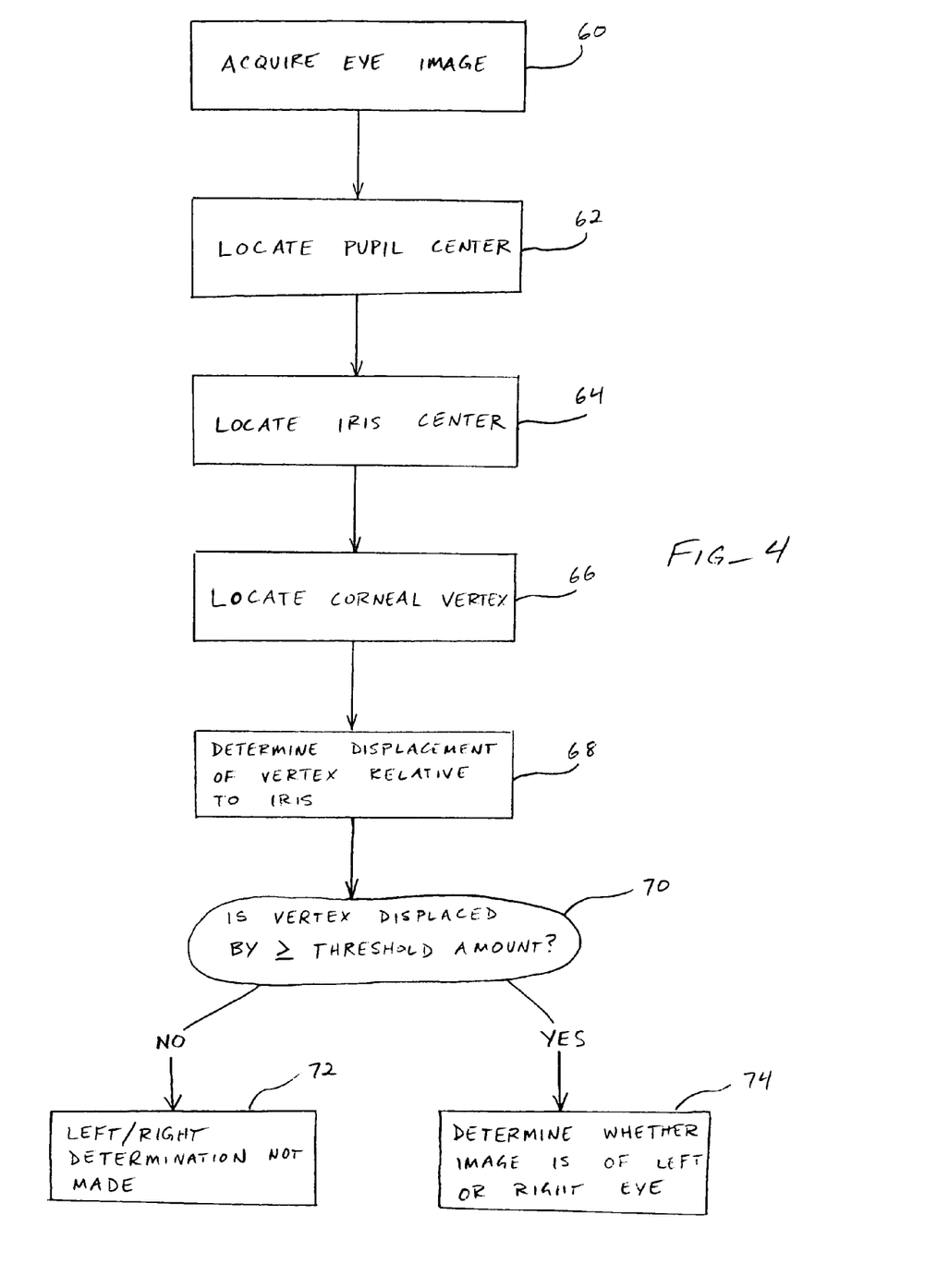
FIG. 4 schematically illustrates a method for distinguishing between right eye images and left eye images according to an embodiment of the present invention.

Referring now to FIG. 4, an exemplary method for determining whether an image is of a left eye or a right eye, as described above, suitably includes a first step of acquiring an image of the eye 60. The image, for example, may be a pupil image. A pupil center may then be located on the pupil image 62. This locating step, as well as many or all subsequent steps, may be achieved in some embodiments via image processing software or other software. Such software may then be used to locate an iris center 64 and a corneal vertex 66 on the pupil image. In some embodiments, locating the corneal vertex 66 may involve first locating one or more reflections on the pupil image caused by infrared illumination used to acquire the image. Once the corneal vertex and iris locations have been determined, the displacement of the vertex relative to the iris may be determined 68. The image processing software or other suitable software then determines whether the displacement of the vertex relative to the iris is greater than or equal to a threshold amount of displacement 70. If not, then no determination is made as to whether the image is of a left or a right eye 72. If the vertex displacement meets or exceeds the threshold, then a determination is made as to whether the image is of a left or a right eye 74. As described above, this determination is made based on the fact that the vertex is almost always nasally displaced relative to the iris center.

When a determination is made as to whether an image is of a left eye or a right eye, such determination may be used as a safety check in a laser eye surgery procedure. For example, the determination as to whether the image is of a left or right eye may be checked against a treatment plan for an eye on which a procedure is about to be performed. If the treatment plan matches the eye that is represented in the image, then the procedure may proceed as planned. If the treatment plan and the image do not match—for example, if the image is of a right eye and the treatment plan is for a left eye—then the laser surgery system may be triggered to provide a warning or alarm that the wrong eye is about to be operated upon. In other embodiments, a mismatch may cause the laser surgery system to shut down temporarily. Any suitable technique for providing a safety check may be incorporated in various embodiments.

In other embodiments, various changes may be made to the method just described while still achieving similar results. For example, instead of locating the iris center, some embodiments may skip that step and compare the corneal vertex location to the pupil center location. In other embodiments, the step of locating the corneal vertex may be skipped, and the displacement of one or more reflections on the pupil image relative to the iris center and/or pupil center may be used to make the left/right determination. In some embodiments, the left/right determination may be made without first comparing the vertex to a threshold amount. And in yet other embodiments, the order of steps may be altered. For example, it may be advantageous in some embodiments to determine a corneal vertex location before an iris center location. Thus, the method described above is but one embodiment and is provided primarily for exemplary purposes.

While the above provides a complete and accurate description of specific embodiments of the invention, a number of changes and adaptations of the present invention may be readily made. Therefore, the scope of the invention is limited solely by the following claims.

What is claimed is:

1. A method comprising:
    aligning an eye with an image capture device by focusing the eye on a fixation target;
    acquiring an image of the aligned eye;
    locating an iris center on the image;
    locating a corneal vertex on the image; and
    determining whether the image is of a left eye or a right eye, based on the location of the corneal vertex relative to the iris center in the image of the aligned eye.

2. A method as in claim 1, further comprising locating a center of a pupil of the eye on the image before locating the center of the iris.

3. A method as in claim 1, wherein locating the corneal vertex comprises locating at least one reflection on the image, wherein the at least one reflection is caused by illuminating the eye while acquiring the image.

4. A method as in claim 3, wherein determining whether the image is of a left eye or a right eye comprises assuming that the at least one reflection is displaced, relative to the iris center, toward a nose of a patient from whom the image was acquired.

5. A method as in claim 4, wherein determining further comprises:
    measuring a displacement of the at least one reflection toward the nose, relative to the iris center; and
    determining whether the image is of the left eye or the right eye, based on the measured displacement.

6. A method as in claim 4, wherein determining further comprises:
    measuring a displacement of the at least one reflection toward the nose, relative to the iris center;
    comparing the measured displacement with a predetermined threshold displacement; and
    determining whether the image is of the left eye or the right eye only if the measured displacement is equal to or greater than the predetermined threshold.

7. A method as in claim 6, further comprising determining the predetermined threshold in response to a sub-population group of a patient having the eye.

8. A method as in claim 1, further comprising obtaining the image by imaging the eye using a wavefront imaging device.

9. A method as in claim 8, wherein obtaining the image comprises obtaining an image of a pupil of the eye.

10. A method of claim 9, further comprising illuminating the eye, including illuminating the pupil using at least one infrared light source disposed near an opening through which the eye image is acquired.

11. A method as in claim 1, further comprising verifying that a correct eye has been selected on which to perform a laser eye surgery procedure, based on the determination of whether the image is of a left eye or a right eye.

12. A method as in claim 1, further comprising providing a warning to a user of a laser eye surgery system before the system is used to perform a laser eye surgery procedure on an incorrect eye, wherein the warning is based on the determination of whether the image is of a left eye or a right eye.

13. A method as in claim 1, further comprising performing a customized laser eye surgery procedure on the eye, based on the determination of whether the image is of a left eye or a right eye.

14. A method of performing laser eye surgery, the method comprising:
    aligning the eye with a wavefront measurement system by focusing the eye on a fixation target;
    acquiring a wavefront measurement of the aligned eye;
    obtaining an image of the eye during the wavefront measurement while the eye is aligned with the wavefront measurement system;
    generating a treatment for the eye based on the wavefront measurement;
    determining whether the image is of a left eye or a right eye, based on nasally-directed displacement of a corneal vertex relative to an iris center on the image of the eye aligned with the wavefront measurement system; and
    verifying that a correct eye has been selected on which to perform a laser eye surgery procedure, based on the determination of whether the image is of a left eye or a right eye.

15. A method as in claim 14, wherein determining whether the image of the eye is of a left eye or a right eye comprises:
    locating the iris center on the image;
    locating the corneal vertex on the image; and
    comparing the location of the corneal vertex to the location of the iris center.

16. A method as in claim 15, wherein locating the corneal vertex comprises locating at least one reflection on the image, wherein the at least one reflection is caused by illuminating the eye while acquiring the image.

17. A method as in claim 16, wherein determining whether the image is of a left eye or a right eye comprises assuming that the at least one reflection is displaced, relative to the iris center, toward a nose of a patient from whom the image was acquired.

18. A method as in claim 17, wherein determining further comprises:
   measuring a displacement of the at least one reflection toward the nose, relative to the iris center; and
   determining whether the image is of the left eye or the right eye, based on the measured displacement.

19. A method as in claim 17, wherein determining further comprises:
   measuring a displacement of the at least one reflection toward the nose, relative to the iris center;
   comparing the measured displacement with a predetermined threshold displacement; and
   determining whether the image is of the left eye or the right eye only if the measured displacement is equal to or greater than the predetermined threshold.

20. A method as in claim 15, further comprising locating a center of a pupil of the eye on the image before locating the iris center.

21. A method as in claim 14, further comprising illuminating the eye before obtaining the image of the eye.

22. A method as in claim 21, illuminating the eye comprises illuminating with at least one infrared light source.

23. A method as in claim 22, wherein illuminating the eye comprises illuminating a pupil of the eye with at least two infrared light emitting diodes disposed near an opening through which the image is acquired.

24. A method as in claim 14, wherein obtaining the image comprises imaging the eye using a wavefront imaging device.

25. A method as in claim 24, wherein obtaining the image comprises obtaining an image of a pupil of the eye.

* * * * *